(12) United States Patent (10) Patent No.: US 8,105,834 B2
Chancellor et al. (45) Date of Patent: Jan. 31, 2012

(54) MUSCLE DERIVED CELLS FOR THE TREATMENT OF URINARY TRACT PATHOLOGIES AND METHODS OF MAKING AND USING SAME

(75) Inventors: Michael B. Chancellor, Pittsburgh, PA (US); Ronald Jankowski, Pittsburgh, PA (US); Ryan Pruchnic, Pittsburgh, PA (US); Johnny Huard, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1056 days.

(21) Appl. No.: 12/013,076

(22) Filed: Jan. 11, 2008

(65) Prior Publication Data

US 2009/0004153 A1 Jan. 1, 2009

Related U.S. Application Data

(60) Provisional application No. 60/884,478, filed on Jan. 11, 2007.

(51) Int. Cl.
*C12N 5/02* (2006.01)
*C12N 5/071* (2006.01)
(52) U.S. Cl. ................... 435/383; 435/378; 435/366
(58) Field of Classification Search ............... 435/383, 435/378, 366
See application file for complete search history.

(56) References Cited

U.S. PATENT DOCUMENTS

| 4,424,208 | A | 1/1984 | Wallace et al. |
| 4,965,353 | A | 10/1990 | Della Valle et al. |
| 5,053,050 | A | 10/1991 | Itay |
| 5,130,141 | A | 7/1992 | Law et al. |
| 5,206,028 | A | 4/1993 | Li |
| 5,336,263 | A | 8/1994 | Ersek et al. |
| 5,516,532 | A | 5/1996 | Atala et al. |
| 5,538,722 | A | 7/1996 | Blau et al. ................ 424/93.21 |

(Continued)

FOREIGN PATENT DOCUMENTS

WO WO 91/07992 6/1991

(Continued)

OTHER PUBLICATIONS

Berjukow et al., "Membrane properties of single muscle cells of the rhabdosphincter of the male urethra", Prostate (2004), 58(3): 238-247.

(Continued)

*Primary Examiner* — Rosanne Kosson
(74) *Attorney, Agent, or Firm* — Mintz Levin Cohn Ferris Glovsky and Popeo, P.C.; Ivor R. Elrifi; Christina K. Stock (57) ABSTRACT

The present invention provides muscle-derived progenitor cells that show long-term survival following transplantation into body tissues and which can augment soft tissue following introduction (e.g. via injection, transplantation, or implantation) into a site of soft tissue. Also provided are methods of isolating muscle-derived progenitor cells, and methods of genetically modifying the cells for gene transfer therapy. The invention further provides methods of using compositions comprising muscle-derived progenitor cells for the augmentation and bulking of mammalian, including human, soft tissues in the treatment of various functional conditions, including malformation, injury, weakness, disease, or dysfunction. In particular, the present invention provides treatments and amelioration for urinary incontinence and other urinary tract pathologies.

15 Claims, 3 Drawing Sheets
(3 of 3 Drawing Sheet(s) Filed in Color)

U.S. PATENT DOCUMENTS

| | | | |
|---|---|---|---|
| 5,594,032 | A | 1/1997 | Gonzalez-Cadavid et al. |
| 5,667,778 | A | 9/1997 | Atala |
| 5,833,978 | A | 11/1998 | Tremblay |
| 5,858,351 | A | 1/1999 | Podsakoff et al. |
| 5,858,390 | A | 1/1999 | Boss |
| 5,876,447 | A | 3/1999 | Arnett |
| 6,001,654 | A | 12/1999 | Anderson et al. |
| 6,099,832 | A | 8/2000 | Mickle et al. |
| 6,261,832 | B1 | 7/2001 | Law |
| 6,866,842 | B1 * | 3/2005 | Chancellor et al. .......... 424/93.1 |
| 2005/0265978 | A1 | 12/2005 | Chancellor et al. |

FOREIGN PATENT DOCUMENTS

| | | |
|---|---|---|
| WO | WO 94/07999 | 4/1994 |
| WO | WO 94/21299 | 9/1994 |
| WO | WO 96/18303 | 6/1996 |
| WO | WO 98/36055 | 8/1998 |
| WO | WO 98/44142 | 10/1998 |
| WO | WO 98/54301 | 12/1998 |
| WO | WO 99/47163 | 9/1999 |
| WO | WO-9946366 A1 | 9/1999 |
| WO | WO 99/56785 | 11/1999 |
| WO | WO 99/56786 | 11/1999 |
| WO | 00/17322 A | 3/2000 |
| WO | 00/29552 A | 5/2000 |
| WO | WO 01/19966 | 3/2001 |
| WO | WO 01/78754 | 10/2001 |
| WO | WO 02/067887 | 9/2002 |
| WO | WO 2009/045506 | 4/2009 |

OTHER PUBLICATIONS

Torrente et al. (2001), "Intraarterial Injection of Muscle-derived CD34±Sca-;1+ Stem Cells Restores Dystrophin in mdx Mice", J of Cell Biology, 152(2):335-348.
Abrams et al., 2002, Neurourol Urodyn 2:167-178.
Acsadi et al., 1994, Hum. Mol. Genet 3:579-584.
Andrews et al., 1986, Blood 67:842-845.
Ashman, 1999, Int. J. Biochem. Cell. Biol. 31:1037-1051.
Berman et al., 1997, J. Urol. 157:122-124.
Blanton et al., 1999, Muscle Nerve 22:43-50.
Cannon et al., 2003, Urology 62:958-963.
Civin et al., 1984, J. Immunol. 133:157-165.
Dominov et al., 1998, J. Cell Biol. 142:537-544.
Faustman et al., 1991, Science 252:1700-1702.
Fina et al, 1990, Blood 75:2417-2426.
Irintchev et al., 1994, Development Dynamics 199:326-337.
Katagiri et al., 1994, J. Cell Biol. 127:1755-1766.
Koretzky, 1993, FASEB J. 7:420-426.
Lee et al., 2003, Int Urogynecol J Pelvic Floor Dysfunct 14: 31-37; discussion 37.
Lipton et al., 1979, Science 205:1292-1294.
Miller et al., 1999, Curr. Top. Dev. Biol. 43:191-219.
Morgan et al., 1988, J. Neural. Sci. 86:137-147.
Osawa et al., 1996, J. Immunol. 156:3207-3214.
Partridge et al., 1978, Nature 273:306-308.
Partridge et al., 1989, Nature 337:176-179.
Price et al., 1987, Proc. Natl. Acad. Sci. USA, 84:156-160.
Simmons et al., 1991, Blood 78:2848-2853.
Van de Rijn et al., 1989, Proc. Natl. Acad. Sci. USA 86:4634-4638.
Watt et al., 1984, Clin. Exp. Immunol. 55:419-426.
Webster et al., 1988, Exp. Cell. Res. 174:252 265.
Ziegler et al., 1999, Science 285:1553-1558.
Kaufman et al. (1988), PNAS, 85:9606-9610.
Office Action issued for U.S. Appl. No. 11/505,735, Mail Date: Sep. 9, 2009.
Alden et al., (1999). "In Vivo Endochondral Bone Formation Using a Bone Morphogenetic Protein 2 Adenoviral Vector", Hum. Gene Ther., 10:2245-2253.
Anderson (1998). "Human gene therapy", Nature, 392:25-30.
Anwer et al., (1998). "Systemic Effect of Human Growth Hormone After Intramuscular Injection of a Single Dose of a Muscle-Specific Gene Medicine", Hum. Gene Ther., 9:659-670.
Arcila et al., (1997). "Mass and Functional Capacity of Regenerating Muscle Is Enhanced by Myoblast Transfer", J. Neurobiol., 33:185-198.
Atkins et al., (1999). "Intracardiac Transplantation of Skeletal Myoblasts Yields Two Populations of Striated Cells In Situ", Ann. Thorac. Surg., 67:124-129.
Atkins et al., (1999). "Myogenic Cell Transplantation Improves in Vivo Regional Performance in Infarcted Rabbit Myocardium", J. Heart Lung Transplant., 18:1173-1180.
Bandara et al., (1993). "Intraarticular expression of biologically active interleukin 1-receptor-antagonist protein by ex vivo gene transfer", Proc. Natl. Acad. Sci., 90:10764-10768.
Baroffio et al., (1996). "Identification of self-renewing myoblasts in the progeny of single human muscle satellite cells", Differentiation, 60:47-57.
Barr & Leiden (1991). "Systemic Delivery of Recombinant Proteins by Genetically Modified Myoblasts", Science, 254:1507-1509.
Beauchamp et al., (1999). "Dynamics of Myoblast Transplantation Reveal a Discrete Minority of Precursors with Stem Cell-like Properties as the Myogenic Source", J. Cell Biol., 144:1113-1122.
Chancellor et al., (2001). "Gene therapy strategies for urological dysfunction", Trends Mol. Med., 7(7):301-306.
Dalle et al., (1999). "Improvement of mouse beta-thalassemia upon erythropoietin delivery by encapsulated myoblasts", Gene Ther., 6:157-161.
Dana et al., (1998). "Interleukin-1 Receptor Antagonist Suppresses Langerhans Cell Activity and Promotes Ocular Immune Privilege", Investigative Ophthalmology & Visual Science, 39:70-77.
Database accession No. EMB-1995233867, (1995). "Genuine stress urinary incontinence with low urethral pressure: Five-year follow-up after the Ball-Burch procedure", Journal of Reproductive Medicine for the Obstetrician and Gynecologist, 40(7):503-506.
Day et al., (1997). "Myoblast-Mediated Gene Transfer to the Joint", J. of Orthopedic Research, 15:894-903.
Deasy et al., (2002). "Gene therapy and tissue engineering based on muscle-derived stem cells", Current Opinion in Molecular Therapeutics, 4:382-389.
Dhawan et al., (1992). "Systemic Delivery of Human Growth Hormone by Injection of Genetically Engineered Myoblasts", Science, 254:1509-1512.
European Search Report, Application No. EP08169379.8, Date: Mar. 9, 2009.
Ferrari et al., (1998). "Muscle Regeneration by Bone Marrow-Derived Myogenic Progenitors", Science, 279:1528-1530.
Friedmann (2000). "Principles for Human Gene Therapy Studies", Science, 287(5461):2163-2165.
Garban et al., (1997). "Cloning of Rat and Human Inducible Penile Nitric Oxide Synthase. Application for Gene Therapy of Erectile Dysfunction", Biol. Reprod., 56(4):954-963.
Grinnell A. D., (1994). "Trophic Interaction Between Nerve and Muscle", Myology Ed. 2, A. G. Engel & C. F. Armstrong, McGraw-Hill, Inc., 303-304.
Gros et al., (1999). "Insulin Production by Engineered Muscle Cells", Hum. Gene Ther., 10:1207-1217.
Gross et al., (1999). "Muscle Precursor Cells Injected into Irradiated mdx Mouse Muscle Persistent After Serial Injury", Muscle & Nerve, 22:174-185.
Gussoni et al., (1992). "Normal dystrophin transcripts detected in Duchenne muscular dystrophy patients after myoblast transplantation", Nature, 356:435-438.
Gussoni et al., (1999). "Dystrophin expression in the mdx mouse restored by stem cell transplantation", Nature, 401:390-394.
Hortelano et al., (1999). "Persistent Delivery of Factor IX in Mice: Gene Therapy for Hemophilia Using Implantable Microcapsules", Hum. Gene Ther., 10:1281-1288.
Huard et al. (1999), "Differentiation of Primary Myoblast Injection into the Lower Urinary Tract; Creation of Detrusor Cellular Myoplasty", J Urology, 161(4S)Supplement:66 (Abstract 248).
Huard et al., (1992). "Human Myoblast Transplantation: Preliminary Results of 4 Cases", Muscle & Nerve, 15:550-560.
Huard et al., (1994). "High Efficiency of Muscle Regeneration after Human Myoblast Clone Transplantation in SCID Mice", J. Clin. Invest., 93:586-599.

Huard et al., (1994). "Human Myoblast Transplantation in Immunodeficient and Immunosuppressed Mice: Evidence of Rejection", Muscle & Nerve, 17:224-234.
Huard et al., (1995). "The route of administration is a major determinant of the transduction efficiency of rat tissues by adenoviral recombinants", Gene Therapy, 2:107-115.
Huard et al., (1998). "Myoblast Injection into the Bladder Wall: A Possible Method of Modulating Detrusor Contractility and Cell-Medicated Gene Therapy for Bladder Dysfunction", J. Urology, 159(5S)Supplement:16 (Abstract 62).
Huard et al., (1998). "Nitric oxide synthases (NOS) Gene Therapy for Erectile Dysfunction: Comparison between Plasmid, Adenovirus and Adenovirus Transduced Myoblast Vectors", J. Urology, 159:90 (Abstract 342).
Huard et al., (2002). "Muscle-derived cell-mediated ex vivo gene therapy for urological dysfunction", Gene Ther., 9:1617-1626.
International Search Report and Written Opinion, Application No. PCT/US2008/011458, Date: Feb. 17, 2008.
Jackson et al., (1999). "Hematopoietic potential of stem cells isolated from murine skeletal muscle", PNAS, 96(25):14482-14486.
Jankowski et al., (2001). "Flow Cytometric Characterization of Myogenic Cell Populations Obtained via the Preplate Technique: Potential for Rapid Isolation of Muscle-Derived Stem Cells", Human Gene Therapy, 12:619-628.
Jiao et al., (1992). "Intracerebral transplants of primary muscle cells: a potential 'platform' for transgene expression in the brain", Brain Research, 575:143-147.
Jung et al., (1999). "Urethral Afferent Nerve Activity Affects the Micturition Reflex; Implication for the Relationship between Stress Incontinence and Detrusor Instability", J. Urology, 162(1):204-212.
Karpati et al., (1993). "Myoblast Transfer in Duchenne Muscular Dystrophy", Ann. Neurol., 34:8-17.
Kasemkijwattana et al., (1998). "Development of Approaches to Improve the Healing Following Muscle Contusion", Cell Transplantation, 7(6):585-598.
Kuby (1994). "Transplantation Immunology", Immunology, 2nd Ed., WH Freeman Company, pp. 559-560.
Ledley (1996). "Pharmaceutical Approach to Somatic Gene Therapy", Pharmaceutical Research, 13(11):1595-1614.
Lee et al., (2000). "Clonal Isolation of Muscle-derived Cells Capable of Enhancing Muscle Regeneration and Bone Healing", J. Cell Biol., 150(5):1085-1099.
Lee et al., (2001). "Urethral Atrophy Incontinence Following Artificial Sphincter Placement: Is Cuff Downsizing Effective?", J. Urology (Suppl.), 165:254 (Abstract 1033).
Lynch et al., (1992). "Long-term expression of human adenosine deaminase in vascular smooth muscle cells of rats: A model for gene therapy", Proc. Natl. Acad. Sci. USA, 89:1138-1142.
Madeiro et al., (2002). "Effects of the association of androgen/estrogen on the bladder and urethra of castrated rats", Clin. Exp. Obst. & Gyn., XXIX(2):117-120.
Martini et al., (1995). "Integration with Other Systems", Anatomy and Physiology, 3rd Ed., Simon & Schuster Company, p. 315.
Moisset et al., (1998). "Successful Transplantation of Genetically Corrected DMD Myoblasts Following ex Vivo Transduction with the Dystrophin Minigene", Biochem. Biophys. Res. Commun., 247:94-99.
Moisset et al., (1998). "Expression of human dystrophin following the transplantation of genetically modified mdx myoblasts", Gene Ther., 5:1340-1346.
Murry et al., (1996). "Skeletal Myoblast Transplantation for Repair of Myocardial Necrosis", J. Clin. Invest., 98:2512-2523.
Musgrave et al., (1998). "Muscle-based tissue engineering for the musculoskeletal system", Gene Therapy & Molecular Biology, 3:1-15.
Newman et al., (2003). "Stress Urinary Incontinence in Women", Am. J. Nurs., 103(8):46-55.
Nurcombe et al., (1985). "Motoneurone Survival and Neuritic Outgrowth Promoted by Different Cell Types in Embryonic Muscle", Developmental Brain Research, 21:49-60 (Abstract).
Partridge and Davies, (1995). "Myoblast-based gene therapies", Brit. Med. Bulletin, 51:123-137.
Pittenger et al., (1999). "Multilineage Potential of Adult Human Mesenchymal Stem Cells", Science, 284:143-147.
Qu et al., (1998). "Development of Approaches to Improve Cell Survival in Myoblast Transfer Therapy", J. Cell Biol., 142(5):1257-1267.
Qu et al., (1999). "Identification of muscle-derived stem cells", Molec. Biol. Of the Cell, 10:246a.
Rando et al., (1994). "Primary Mouse Myoblast Purification, Characterization, and Transplantation for Cell-mediated Gene Therapy", J. Cell Biol., 125(6):1275-1287.
Regulier et al., (1998). "Continuous delivery of human and mouse erythropoietin in mice by genetically engineered polymer encapsulated myoblasts", Gene Ther., 5:1014-1022.
Richler et al., (1970). "The in Vitro Cultivation and Differentiation Capacities of Myogenic Cell Lines", Developmental Biology, 23:1-22.
Roman et al., (1992). "Circulating Human or Canine Factor IX from Retrovirally Transduced Primary Myoblasts and Established Myoblast Cell Lines Grafted into Murine Skeletal Muscle", Somat. Cell. Mol. Genet., 18:247-258.
Rosenberg et al., (2000). "Gene Therapist, Heal Thyself", Science, 287:1751.
Sanes et al., (1986). "Adult Stem Cells: The Therapeutic Potential of Skeletal Muscle", EMBO J., 5:3133.
Saini et al., (2006). "Use of a recombinant retrovirus to study post-implantation cell lineage in mouse embryos", Curr. Stem Cell Res. Ther., 1(2):157-171.
Seale et al., (2000). "A New Look at the Origin, Function, and 'Stem-Cell' Status of Muscle Satellite Cells", Developmental Biology, 218:115-124.
Smith et al., (1997). "Stable Integration of an mdx Skeletal Muscle Cell Line into Dystrophic (mdx) Skeletal Muscle: Evidence for Stem Cell Status", Cell Growth and Differentiation, 8(8):927-934.
Somogyi et al., (1999), "A precise, localized bladder injury model to investigate the effect of myoblast injection on bladder contractility", J Urology, 161(4S)Supplement:43 (Abstract 158).
Spindler et al., (1995). "Regional Mitogenic Response of the Meniscus to Platelet-Derived Growth Factor (PDGF-AB)", J. of Orthopedic Research, 13:201-207.
Tirney et al., (2001). "Nitric Oxide Synthase Gene Therapy for Erectile Dysfunction: Comparison of Plasmid, Adenovirus, and Adenovirus-Transduced Myoblast Vectors", Mol. Urol. Spring, 5(1):37-43.
Tirney et al., (1998), "Myoblast Periuretheral Injection for the Treatment of Stress Urinary Incontinence", J. Urology, 159(5S)Supplement:327 (Abstract 1256).
Tremblay et al., (1993). "Results of triple blind clinical study of myoblast transplantations without immunosuppressive treatment in young boyx with Duchenne muscular dystrophy", Cell Transplantation, 2:99-112.
Tremblay et al., (1997). "Myoblast Transplantation: a Brief Review of the Problems and of Some Solutions", Basic Appl. Myol., 7(3& 4):221-230.
Tzeng et al., (1996). "Vascular inducible nitric oxide synthase gene therapy: Requirement for guanosine triphosphate cyclohydrolase I", Surgery, 120(2):315-321.
Vandenburgh (1996). "Tissue-Engineered Skeletal Muscle Organoids for Reversible Gene Therapy", Hum. Gene Ther., 7:2195-2200.
Verma (2000). "Gene Therapy: Beyond 2000", Mol. Ther., 1:493.
Wang et al., (1997). "Persistent Systemic Production of Human Factor IX in Mice by Skeletal Myoblast-Mediated Gene Transfer: Feasibility of Repeat Application to Obtain Therapeutic Levels", Blood, 90:1075-1082.
Yamanishi et al., (2002). "Identification of Beta-Adrenoceptor Subtypes in Lower Urinary Tract of the Female PIG", J. Urology, 168:2706-2710.
Yao et al., (1994). "Primary myoblast-mediated gene transfer: persistent expression of human factor IX in mice", Gene Ther., 1:99-107.
Yokoyama et al. (1999), "Primary Myoblast Injection into the Urethra and Bladder as a Potential Treatment of Stress Urinary Incontinence and Impaired Detrusor Contractility; Long-Term Survival Without Significant Cytotoxicity", J Urology, 161(4S)Supplement:307 (Abstract 1182).

Yokoyama et al., (1999). "Gene therapy as a potential treatment for BPH: Injection of myoblast-adenovirus transfected with human inducible nitric oxide synthase (iNOS) into the proximal urethra", J. Urology, 161(4S)Supplement:305 (Abstract 1775).

Yokoyama et al., (2000). "Myoblast therapy for stress urinary incontinence and bladder dysfunction", World J. Urology, 18:56-61.

Yokoyama et al., (2001). "Persistence and Survival of Autologous Muscle Derived Cells Versus Bovine Collagen as Potential Treatment of Stress Urinary Incontinence", J. Urology, 165:271-276.

Yokoyama et al., (2001). "Muscle-derived cell transplantation and differentiation into lower urinary tract smooth muscle", Tissue Engineering, 7(4):395-404.

Yokoyama et al., (2001). "Autologous Primary Muscle-Derived Cells Transfer into the Lower Urinary Tract", Urology, 57(4):826-831.

Yoshida et al., (1998). "Cell heterogeneity upon myogenic differentiation: Down-regulation of MyoD and Myf-5 generates 'reserve cells'", J. Cell Science. 111:769-779.

Young et al., (1993). "Pluripotent mesenchymal stem cells reside within avian connective tissue matrices", In vitro Cell Dev. Biol., 29A:723-736.

Young et al., (1995). "Mesenchymal Stem Cells Reside Within the Connective Tissues of Many Organs", Dev. Dynam., 202:137-144.

Crisan et al., "Identification, purification and characterization of a novel population of cd146+cd133+ myogenic cells in human skeletal muscle", The Orthopaedic Research Society (ORS) 53rd Annual Meeting (Feb. 12-14, 2007), San Diego, CA (Paper No. 0040).

Ding et al., "Bone marrow stromal cells as a vehicle for gene transfer", Gene Therapy (1999), 6(9):1611-1616.

Deasy et al., "A role for cell sex in stem cell mediated skeletal muscle regeneration: female cells have higher muscle regeneration efficiency", J. Cell Biol. (2007), 177(1):73-86.

Oshima et al.., "Skeletal muscle stem cells acquire a cardiac phenotype and display a superior ability for cardiac repair when compared to satellite cells", The Japanese Journal of Thoracic and Cardiovascular Surgery, 52(Suppl 2004):192.

Oshima et al., "Muscle stem cells provide superior infarct repair when compared with myoblasts", Molecular Therapy (2005), 11(Suppl 1):920.

Oshima et. al., "Differential myocardial infarct repair with muscle stem cells compared to myoblasts", Mol. Ther. (2005), 12(6):1130-41.

Payne et al., "Muscle-derived stem cells express a cardiac phenotype upon transplantation into the dystrophic murine heart", American Heart Association Conference on Molecular Mechanisms of Growth, Death and Regeneration in the Myocardium (Aug. 2003), Snowbird, UT, 9: P42.

Payne et. al., "Regeneration of dystrophin-expressing myocytes in the mdx heart by skeletal muscle stem cells", Gene Ther. (2005), 12(16):1264-74.

Payne et al., "A relationship between VEGF, angiogenesis and cardiac repair after muscle stem cell transplantation into ischemic hearts", Journal of the American College of Cardiology (2007), 50(17):1677-84.

Payne et al., "VEGF secretion by skeletal muscle-derived stem cells induces neovascularization, prevents remodeling, and improves function in ischemic heart", Circulation Research (2006), 99(5):P17.

Payne et al., "Muscle stem cells deliver dystrophin and adopt a cardiac phenotype through both differentiation and fusion in the dystrophic (mdx) heart", Mol Ther (2004), 9(Suppl 1):930.

Payne et al., "Muscle stem cells genetically modified to express a VEGF antagonist display an impaired ability for cardiac repair", Mol Ther (2005), 11(Suppl 1):923.

Urish et al., "Muscle stem cells' high regenerative capacity correlates with a high resistance to stress", The Orthopaedic Research Society 52nd Annual Meeting (Mar. 19-22, 2006), Chicago, IL (Paper No. 0337).

Urish et al., "The role of resistance to inflammation and oxidative stress in muscle stem cells' increased regenerative capacity", International Society for Stem Cell Research (Jun. 29-Jul. 1, 2006), Toronto, Canada.

Urish et al., "Oxidative stress plays a major role in the differential repair of skeletal and cardiac muscle between muscle stem cells and myoblasts", The Orthopaedic Research Society (ORS) 53rd Annual Meeting (Feb. 12-14, 2007), San Diego, CA (Paper No. 1225).

Zheng et al., "Multi-potency of myo-endothelial clones isolated from adult human skeletal muscle. NIRA nominee", The Orthopaedic Research Society (ORS) 53rd Annual Meeting (Feb. 12-14, 2007), San Diego, CA (Paper No. 0421).

Chancellor et al., (2000), Neurourology and Urodynamics, 19(3):279-287.

Supplementary European Search Report, Appl. No. EP 02706457, Mailed on May 27, 2009.

Fukuda et al., (2000), Tanpakushita Kakusan Kouso (Protein, Nucleic Acid and Enzyme) 45(13), 2078-2084.

Ikada (2001), "Tissue Engineering—Toward Establishing of Basic Technology and Clinical Applications," Kagaku-Dojin Publishing Co., Inc. pp. 183-191.

Pre-Appeal Examination Report, Appl. No. JP2002-567239, Date: Oct. 22, 2007 (with English Translation).

Japanese Office Action, Application No. JP2002-567239, Date: Feb. 7, 2007 (with English Translation).

* cited by examiner

MUSCLE DERIVED CELLS FOR THE TREATMENT OF URINARY TRACT PATHOLOGIES AND METHODS OF MAKING AND USING SAME

RELATED APPLICATIONS

This application claims priority from U.S. Provisional Application No. 60/884,478, filed on Jan. 11, 2007, which is incorporated herein in its entirety.

FIELD OF THE INVENTION

The present invention relates to muscle-derived progenitor cells (MDC) and compositions of MDCs and their use in the augmentation of body tissues, particularly soft tissue like urethral and periurethral muscle. In particular, the present invention relates to muscle-derived progenitor cells that show long-term survival following introduction into soft tissues, methods of isolating MDCs, and methods of using MDC-containing compositions for the augmentation of human or animal soft tissues, including epithelial, adipose, nerve, organ, muscle, ligament, and cartilage tissue. The invention also relates to novel uses of muscle-derived progenitor cells for the treatment of functional conditions, such as stress urinary incontinence or urinary incontinence.

BACKGROUND OF THE INVENTION

Stress urinary incontinence (SUI) is a common condition and is characterized as the involuntary leakage of urine on effort, exertion, sneezing or coughing. (Abrams P, et al. *Neurourol Urodyn* 2002; 21(2): 167-178). The etiology of SUI is multifactorial, involving damage and/or functional impairment of muscle and associated nerves that may occur as a result of advancing age, hormonal status, and pelvic floor damage resulting from vaginal child-birth. Due to the multifactorial etiology, a single treatment option, that is not limited in some fashion, does not currently exist.

The use of periurethral injectables as a minimally invasive treatment option, which may be performed on an outpatient basis under local anesthesia. This method of treatment is more cost effective in the near-term, with shorter hospitalization, reduced operating room time, and generally fewer complications when compared with invasive surgical approaches such as bladder neck suspension. (Berman C J, et al. *J Urol* 1997; 157(1): 122-124). However, it has disadvantages such as need for multiple injections due to loss of the long-term bulking effect owing to degradation, reabsorption, and/or migration, as well as other impediments such as bladder outlet obstruction and allergic reactions. Thus, there is a need for other, different urinary augmentation materials that are long-lasting, compatible with a wide range of host tissues, and which cause minimal inflammation, scarring, and/or stiffening of the tissues surrounding the implant site.

Muscle derived cells isolated from rats have shown some success models for urinary incontinence. (Cannon T W, et al. *Urology* 2003; 62(5): 958-963 and Lee J Y et al. *Int Urogynecol J Pelvic Floor Dysfunct* 2003; 14(1): 31-37; discussion 37). The instant invention provides the use of human skeletal muscle derived cells (MDC) as an injectable treatment for SUI, and other urinary tract pathologies.

SUMMARY OF THE INVENTION

It is an object of the present invention to provide novel human muscle-derived progenitor cells (MDCs) and human MDC compositions exhibiting long-term survival following transplantation. The MDCs of this invention and compositions containing the MDCs comprise early progenitor muscle cells, i.e., muscle-derived stem cells, that express progenitor cell markers, such as desmin, M-cadherin, MyoD, myogenin, CD34, and Bcl-2. In addition, these early progenitor muscle cells express the Flk-1, Sca-1, MNF, and c-met cell markers, but do not express the CD45 or c-Kit cell markers.

It is another object of the present invention to provide methods for isolating and enriching human muscle-derived progenitor cells from a starting muscle cell population. These methods result in the enrichment of human MDCs that have long-term survivability after transplantation or introduction into a site of soft tissue. The MDC population according to the present invention is particularly enriched with cells that express progenitor cell markers, such as desmin, M-cadherin, MyoD, myogenin, CD34, and Bcl-2. This MDC population also expresses the Flk-1, Sca-1, MNF, and c-met cell markers, but does not express the CD45 or c-Kit cell markers.

It is yet another object of the present invention to provide methods of using MDCs and compositions comprising MDCs for the augmentation of muscle soft tissue, or non-muscle soft tissue, including smooth muscle, and various organ tissues, without the need for polymer carriers or special culture media for transplantation. Such methods include the administration of MDC compositions by introduction into soft tissue, for example by direct injection into tissue, or by systemic distribution of the compositions. Preferably, soft tissue includes non-bone body tissues. More preferably, soft tissue includes non-striated muscle and non-bone body tissues. Most preferably, soft tissue includes non-muscle, non-bone body tissues. As used herein, augmentation refers to filling, bulking, supporting, enlarging, extending, or increasing the size or mass of body tissue.

It is another object of the present invention to provide methods of augmenting soft tissue, either muscle-derived soft tissue, or non-muscle-derived soft tissue, following injury, wounding, surgeries, traumas, non-traumas, or other procedures that result in fissures, openings, depressions, wounds, and the like, in the skin or in internal soft tissues or organs.

It is yet another object of the present invention to provide human MDC-based treatments for urinary tract disease and associated symptoms. Pharmaceutical compositions comprising MDCs and compositions comprising MDCs may be used for the treatment of urinary tract pathologies. These pharmaceutical compositions comprise isolated human MDCs. These MDCs may be subsequently expanded by cell culture after isolation. In one embodiment of the invention, these MDCs are frozen prior to delivery to a subject in need of the pharmaceutical composition.

In one embodiment, when the human MDCs and compositions thereof are used to treat urinary incontinence they are injected directly into the urethra. Preferably, they may be injected into the periurethral muscle In another embodiment, human MDCs and compositions thereof are used to improve at least one symptom of urinary tract disease. These symptoms include urinary incontinence, urinary tract infection, frequent urination, painful urination, burning sensation when urinating, fatigue, tremor, cloudy urine, blood in urine, and kidney infection.

Human MDCs are isolated from a biopsy of skeletal muscle. In one embodiment, the skeletal muscle from the biopsy may be stored for 1-6 days. In one aspect of this embodiment, the skeletal muscle from the biopsy is stored at 4° C. The MDCs are then isolated using the pre-plate or the single plate technique.

Using the pre-plate technique, a suspension of skeletal muscle cells from skeletal muscle tissue is plated in a first container to which fibroblast cells of the skeletal muscle cell suspension adhere. Non-adherent cells are then re-plated in a second container, wherein the step of re-plating is after 15-20% of cells have adhered to the first container. This replating step must be repeated at least once. The MDCs are thereby isolated and may be administered to the esophagus of the mammalian subject.

Using the single plate technique, the cells are minced, and digested using a collagenase, dispase, another enzyme or a combination of enzymes. After washing the enzyme from the cells, the cells are cultured in a flask in culture medium for between about 30 and about 120 minutes. During this period of time, the "rapidly adhering cells" stick to the walls of the flask or container, while the "slowly adhering cells" or MDCs remain in suspension. The "slowly adhering cells" are transferred to a second flask or container and cultured therein for a period of 1-3 days. During this second period of time the "slowly adhering cells" or MDCs stick to the walls of the second flask or container.

In another embodiment of the invention, these MDCs are expanded to any number of cells. In a preferred aspect of this embodiment, the cells are expanded in new culture media for between about 10 and 20 days. More preferably, the cells are expanded for 17 days.

The MDCs, whether expanded or not expanded, may be preserved in order to be transported or stored for a period of time before use. In one embodiment, the MDCs are frozen. Preferably, the MDCs are frozen at between about −20 and −90° C. More preferably, the MDCs are frozen at about −80° C. These frozen MDCs are used as a pharmaceutical composition.

Additional objects and advantages afforded by the present invention will be apparent from the detailed description and exemplification hereinbelow.

BRIEF DESCRIPTION OF THE DRAWINGS

The patent or patent application file contains at least one photographic reproduction executed in color. Copies of this patent or patent application with color photographic reproduction(s) will be provided by the U.S. Patent and Trademark Office upon request and payment of the necessary fee.

The appended drawings of the figures are presented to further describe the invention and to assist in its understanding through clarification of its various aspects.

DETAILED DESCRIPTION OF THE INVENTION

The invention provides human MDCs and methods of using such cells to generate tissue with bulking properties that have the potential to improve coaptation and intrinsic sphincter function by remodeling the damaged tissue. The invention further provides methods of treating urinary tract disorders including incontinence and stress urinary incontinence. The isolation of human muscle-derived cells (MDCs) from adult tissue are capable of achieving functional success within an established urethral sphincter injury model.

Muscle-Derived Cells and Compositions

The present invention provides MDCs comprised of early progenitor cells (also termed muscle-derived progenitor cells or muscle-derived stem cells herein) that show long-term survival rates following transplantation into body tissues, preferably soft tissues. To obtain the MDCs of this invention, a muscle explant, preferably skeletal muscle, is obtained from an animal donor, preferably from a mammal, including rats, dogs and humans. This explant serves as a structural and functional syncytium including "rests" of muscle precursor cells (T. A. Partridge et al., 1978, Nature 73:306-8; B. H. Lipton et al., 1979, Science 205:12924).

Cells isolated from primary muscle tissue contain mixture of fibroblasts, myoblasts; adipocytes, hematopoietic, and muscle-derived progenitor cells. The progenitor cells of a muscle-derived population can be enriched using differential adherence characteristics of primary muscle cells on collagen coated tissue flasks, such as described in U.S. Pat. No. 6,866,842 of Chancellor et al. Cells that are slow to adhere tend to be morphologically round, express high levels of desmin, and have the ability to fuse and differentiate into multinucleated myotubes (U.S. Pat. No. 6,866,842 of Chancellor et al.). A subpopulation of these cells was shown to respond to recombinant human bone morphogenic protein 2 (rhBMP-2) In vitro by expressing increased levels of alkaline phosphatase, parathyroid hormone dependent 3',5'-cAMP, and osteogenic lineage and myogenic lineages (U.S. Pat. No. 6,866,842 of Chancellor et al.; T. Katagiri et al., 1994, J. Cell Biol., 127: 1755-1766).

In one embodiment of the invention, a preplating procedure may be used to differentiate rapidly adhering cells from slowly adhering cells (MDCs). In accordance with the present invention, populations of rapidly adhering cells (PP1-4) and slowly adhering, round MDCs (PP6) were isolated and enriched from skeletal muscle explants and tested for the expression of various markers using immunohistochemistry to determine the presence of pluripotent cells among the slowly adhering cells (Example 1; patent application U.S. Ser. No. 09/302,896 of Chancellor et al.). The PP6 cells expressed myogenic markers, including desmin, MyoD, and Myogenin. The PP6 cells also expressed c-met and MNF, two genes which are expressed at an early stage of myogenesis (J. B. Miller et al., 1999, Curr. Top. Dev. Biol. 43:191-219). The PP6 showed a lower percentage of cells expressing M-cadherin, a satellite cell-specific marker (A. Irintchev et al., 1994, Development Dynamics 199:326-337), but a higher percentage of cells expressing Bcl-2, a marker limited to cells in the early stages of myogenesis (J. A. Dominov et al., 1998, J. Cell Biol. 142:537-544). The PP6 cells also expressed CD34, a marker identified with human hematopoietic progenitor cells, as well as stromal cell precursors in bone marrow (R. G. Andrews et al., 1986, Blood 67:842-845; C. I. Civin et al., 1984, J. Immunol. 133:157-165; L. Fina et al, 1990, Blood 75:2417-2426; P. J. Simmons et al., 1991, Blood 78:2848-2853). The PP6 cells also expressed Flk-1, a mouse homologue of human KDR gene which was recently identified as a marker of hematopoietic cells with stem cell-like characteristics (B. L. Ziegler et al., 1999, Science 285:1553-1558). Similarly, the PP6 cells expressed Sca-1, a marker present in hematopoietic cells with stem cell-like characteristics (M. van de Rijn et al., 1989, Proc. Natl. Acad. Sci. USA 86:4634-8; M. Osawa et al., 1996, J. Immunol. 156:3207-14). However, the PP6 cells did not express the CD45 or c-Kit hematopoietic stem cell markers (reviewed in L K. Ashman, 1999, *Int. J. Biochem. Cell. Biol.* 31:1037-51; G. A. Koretzky, 1993, *FASEB J.* 7:420-426).

One embodiment of the present invention is the PP6 population of muscle-derived progenitor cells having the characteristics described herein. These muscle-derived progenitor cells express the desmin, CD34, and Bcl-2 cell markers. In accordance with the present invention, the PP6 cells are isolated by the techniques described herein (Example 1) to obtain a population of muscle-derived progenitor cells that have long-term survivability following transplantation. The PP6 muscle-derived progenitor cell population comprises a significant percentage of cells that express progenitor cell markers such as desmin, CD34, and Bcl-2. In addition, PP6 cells express the Flk-1 and Sca-1 cell markers, but do not express the CD45 or c-Kit markers. Preferably, greater than 95% of the PP6 cells express the desmin, Sca-1, and Flk-1 markers, but do not express the CD45 or c-Kit markers. It is preferred that the PP6 cells are utilized within about 1 day or about 24 hours after the last plating.

In a preferred embodiment, the rapidly adhering cells and slowly adhering cells (MDCs) are separated from each other using a single plating technique. One such technique is described in Example 2. First, cells are provided from a skeletal muscle biopsy. The biopsy need only contain about 100 mg of cells. Biopsies ranging in size from about 50 mg to about 500 mg can be used according to both the pre-plating and single plating methods of the invention. Further biopsies of 50, 100, 110, 120, 130, 140, 150, 200, 250, 300, 400 and 500 mg can be used according to both the pre-plating and single plating methods of the invention.

In a preferred embodiment of the invention, the tissue from the biopsy is then stored for 1 to 7 days. This storage is at a temperature from about room temperature to about 4° C. This waiting period causes the biopsied skeletal muscle tissue to undergo stress. While this stress is not necessary for the isolation of MDCs using this single plate technique, it seems that using the wait period results in a greater yield of MDCs.

Tissue from the biopsies is minced and centrifuged. The pellet is resuspended and digested using a digestion enzyme. Enzymes that may be used include collagenase, dispase or combinations of these enzymes. After digestion, the enzyme is washed off of the cells. The cells are transferred to a flask in culture media for the isolation of the rapidly adhering cells. Many culture media may be used. Particularly preferred culture-media include those that are designed for culture of endothelial cells including Cambrex Endothelial Growth Medium. This medium may be supplemented with other components including fetal bovine serum, IGF-1, bFGF, VEGF, EGF, hydrocortisone, heparin, and/or ascorbic acid. Other media that may be used in the single plating technique include InCell M310F. medium. This medium may be supplemented as described above, or used unsupplemented.

The step for isolation of the rapidly adhering cells may require culture in flask for a period of time from about 30 to about 120 minutes. The rapidly adhering cells adhere to the flask in 30, 40, 50, 60, 70, 80, 90, 100, 110 or 120 minutes. After they adhere, the slowly adhering cells are separated from the rapidly adhering cells by removing the culture media from the flask to which the rapidly adhering cells are attached.

The culture medium removed from this flask is then transferred to a second flask. The cells may be centrifuged and resuspended in culture medium before being transferred to the second flask. The cells are cultured in this second flask for between 1 and 3 days. Preferably, the cells are cultured for two days. During this period of time, the slowly adhering cells (MDCs) adhere to the flask. After the MDCs have adhered, the culture media is removed and new culture media is added so that the MDCs can be expanded in number. The MDCs may be expanded in number by culturing them for from about 10 to about 20 days. The MDCs may be expanded in number by culturing them for 10, 11, 12, 13, 14, 15, 16, 17, 18, 19 or 20 days. Preferably, the MDCs are subject to expansion culture for 17 days.

As an alternative to the pre-plating and single plating methods, the MDCs of the present invention can be isolated by fluorescence-activated cell sorting (FACS) analysis using labeled antibodies against one or more of the cell surface markers expressed by the MDCs (C. Webster et al., 1988, *Exp. Cell. Res.* 174:252-65; J. R. Blanton et al., 1999, *Muscle Nerve* 22:43-50). For example, FACS analysis can be performed using labeled antibodies to directed to CD34, Flk-1, Sca-1, and/or the other cell-surface markers described herein to select a population of PP6-like cells that exhibit long-term survivability when introduced into the host tissue. Also encompassed by the present invention is the use of one or more fluorescence-detection labels, for example, fluorescein or rhodamine, for antibody detection of different cell marker proteins.

Using any of the MDCs isolation methods described above, MDCs that are to be transported, or are not going to be used for a period of time may be preserved using methods known in the art. More specifically, the isolated MDCs may be frozen to a temperature ranging from about −25 to about −90° C. Preferably, the MDCs are frozen at about −80° C., on dry ice for delayed use or transport. The freezing may be done with any cryopreservation medium known in the art.

Muscle-Derived Cell-Based Treatments

In one embodiment of the present invention, the MDCs are isolated from a skeletal muscle source and introduced or transplanted into a muscle or non-muscle soft tissue site of interest, or into bone structures. Advantageously, the MDCs of the present invention are isolated and enriched to contain a large number of progenitor cells showing long-term survival following transplantation. In addition, the muscle-derived progenitor cells of this invention express a number of characteristic cell markers, such desmin, CD34, and Bcl-2. Furthermore, the muscle-derived progenitor cells of this invention express the Sca-1, and Flk-1 cell markers, but do not express the CD45 or c-Kit cell markers.

MDCs and compositions comprising MDCs of the present invention can be used to repair, treat, or ameliorate various aesthetic or functional conditions (e.g. defects) through the augmentation of muscle or non-muscle soft tissues. In particular, such compositions can be used as soft-tissue bulking agents for the treatment of urinary incontinence and other instances of smooth muscle weakness, disease, injury, or dysfunction. In addition, such MDCs and compositions thereof can be used for augmenting soft tissue not associated with injury by adding bulk to a soft tissue area, opening, depression, or void in the absence of disease or trauma, such as for "smoothing". Multiple and successive administrations of MDCs are also embraced by the present invention.

For MDC-based treatments, a skeletal muscle explant is preferably obtained from an autologous or heterologous human or animal source. An autologous animal or human source is more preferred. MDC compositions are then prepared and isolated as described herein. To introduce or transplant the MDCs and/or compositions comprising the MDCs according to the present invention into a human or animal recipient, a suspension of mononucleated muscle cells is prepared. Such suspensions contain concentrations of the muscle-derived progenitor cells of the invention in a physiologically-acceptable carrier, excipient, or diluent. For example, suspensions of MDCs for administering to a subject can comprise $10^8$ to $10^9$ cells/ml in a sterile solution of complete medium modified to contain the subject's serum, as an alternative to fetal bovine serum. Alternatively, MDC suspensions can be in serum-free, sterile solutions, such as cryopreservation solutions (Celox Laboratories, St. Paul, Minn.). The MDC suspensions can then be introduced e.g., via injection, into one or more sites of the donor tissue.

The described cells can be administered as a pharmaceutically or physiologically acceptable preparation or composition containing a physiologically acceptable carrier, excipient, or diluent, and administered to the tissues of the recipient organism of interest, including humans and non-human animals. The MDC-containing composition can be prepared by resuspending the cells in a suitable liquid or solution such as sterile physiological saline or other physiologically acceptable injectable aqueous liquids. The amounts of the components to be used in such compositions can be routinely determined by those having skill in the art.

The MDCs or compositions thereof can be administered by placement of the MDC suspensions onto absorbent or adherent material, i.e., a collagen sponge matrix, and insertion of the MDC-containing material into or onto the site of interest. Alternatively, the MDCs can be administered by parenteral routes of injection, including subcutaneous, intravenous, intramuscular, and intrasternal. Other modes of administration include, but are not limited to, intranasal, intrathecal, intracutaneous, percutaneous, enteral, and sublingual. In one embodiment of the present invention, administration of the MDCs can be mediated by endoscopic surgery.

For injectable administration, the composition is in sterile solution or suspension or can be resuspended in pharmaceutically- and physiologically-acceptable aqueous or oleaginous vehicles, which may contain preservatives, stabilizers, and material for rendering the solution or suspension isotonic with body fluids (i.e. blood) of the recipient. Non-limiting examples of excipients suitable for use include water, phosphate buffered saline, pH 7.4, 0.15 M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as the routes of administration used, are determined on an individual basis, and correspond to the amounts used in similar types of applications or indications known to those of skill in the art.

To optimize transplant success, the closest possible immunological match between donor and recipient is desired. If an autologous source is not available, donor and recipient Class I and Class II histocompatibility antigens can be analyzed to determine the closest match available. This minimizes or eliminates immune rejection and reduces the need for immunosuppressive or immunomodulatory therapy. If required, immunosuppressive or immunomodulatory therapy can be started before, during, and/or after the transplant procedure. For example, cyclosporin A or other immunosuppressive drugs can be administered to the transplant recipient. Immunological tolerance may also be induced prior to transplantation by alternative methods known in the art (D. J. Watt et al., 1984, *Clin. Exp. Immunol.* 55:419; D. Faustman et al., 1991, *Science* 252:1701).

Consistent with the present invention, the MDCs can be administered to body tissues, including epithelial tissue (i.e., skin, lumen, etc.) muscle tissue (i.e. smooth muscle), and various organ tissues such as those organs that are associated with the urological system (i.e., bladder, urethra, ureter, kidneys, etc.).

The number of cells in an MDC suspension and the mode of administration may vary depending on the site and condition being treated. As non-limiting examples, in accordance with the present invention, about $3-5\times10^5$ MDCs are injected for the treatment of urinary incontinence (see Example 3). Consistent with the Examples disclosed herein, a skilled practitioner can modulate the amounts and methods of MDC-based treatments according to requirements, limitations, and/or optimizations determined for each case.

Conditions of the lumen: In another embodiment, the MDCs and compositions thereof according to the present invention have further utility as treatments for conditions of the lumen in an animal or mammal subject, including humans. Specifically, the muscle-derived progenitor cells are used for completely or partially blocking, enhancing, enlarging, sealing, repairing, bulking, or filling various biological lumens or voids within the body. Lumens include, without limitation the urethra. Voids may include, without limitation, various tissue wounds (i.e., loss of muscle and soft tissue bulk due to trauma; destruction of soft tissue due to penetrating projectiles such as a stab wound or bullet wound; loss of soft tissue from disease or tissue death due to surgical removal of the tissue including loss of breast tissue following a mastectomy for breast cancer or loss of muscle tissue following surgery to treat sarcoma, etc.), lesions, fissures, diverticulae, cysts, fistulae, aneurysms, and other undesirable or unwanted depressions or openings that may exist within the body of an animal or mammal, including humans. For the treatment of conditions of the lumen, the MDCs are prepared as disclosed herein and then administered, e.g. via injection or intravenous delivery, to the lumenal tissue to fill or repair the void. The number of MDCs introduced is modulated to repair large or small voids in a soft tissue environment, as required.

Conditions of the sphincter: The MDCs and compositions thereof according to the present invention can also be used for the treatment of a sphincter injury, weakness, disease, or dysfunction in an animal or mammal, including humans. In particular, the MDCs are used to augment tissues of the urinary sphincters. More specifically, the present invention provides soft tissue augmentation treatments for urinary incontinence. For the treatment of sphincter defects, the MDCs are prepared as described herein and then administered to the sphincter tissue, e.g. via injection, to provide additional bulk, filler, or support. The number of MDCs introduced is modulated to provide varying amounts of bulking material as required. For example, about $3-5\times10^5$ MDCs are injected for the treatment of urinary incontinence (see Example 3).

In addition, the MDCs and compositions thereof can be used to affect contractility in smooth muscle tissue, such as urinary or bladder tissue, as example. Thus, the present invention also embraces the use of MDCs of the invention in restoring muscle contraction, and/or ameliorating or overcoming smooth muscle contractility problems.

Genetically Engineered Muscle-Derived Cells

In another aspect of the present invention, the MDCs of this invention may be genetically engineered to contain a nucleic acid sequence(s) encoding one or more active biomolecules, and to express these biomolecules, including proteins, polypeptides, peptides, hormones, metabolites, drugs, enzymes, and the like. Such MDCs may be histocompatible (autologous) or nonhistocompatible (allogeneic) to the recipient, including humans. These cells can serve as long-term local delivery systems for a variety of treatments, for example, urinary incontienence.

Preferred in the present invention are autologous muscle-derived progenitor cells, which will not be recognized as foreign to the recipient. In this regard, the MDCs used for cell-mediated gene transfer or delivery will desirably be matched vis-a-vis the major histocompatibility locus (MHC or HLA in humans). Such MHC or HLA matched cells may be autologous. Alternatively, the cells may be from a person having the same or a similar MHC or HLA antigen profile. The patient may also be tolerized to the allogeneic MHC antigens. The present invention also encompasses the use of cells lacking MHC Class I and/or II antigens, such as described in U.S. Pat. No. 5,538,722.

The MDCs may be genetically engineered by a variety of molecular techniques and methods known to those having skill in the art, for example, transfection, infection, or transduction. Transduction as used herein commonly refers to cells that have been genetically engineered to contain a foreign or heterologous gene via the introduction of a viral or non-viral vector into the cells. Transfection more commonly refers to cells that have been genetically engineered to contain a foreign gene harbored in a plasmid, or non-viral vector. MDCs can be transfected or transduced by different vectors and thus can serve as gene delivery vehicles to transfer the expressed products into muscle.

Although viral vectors are preferred, those having skill in the art will appreciate that the genetic engineering of cells to contain nucleic acid sequences encoding desired proteins or polypeptides, cytokines, and the like, may be carried out by methods known in the art, for example, as described in U.S. Pat. No. 5,538,722, including fusion, transfection, lipofection mediated by the use of liposomes, electroporation, precipitation with DEAE-Dextran or calcium phosphate, particle bombardment (biolistics) with nucleic acid-coated particles (e.g., gold particles), microinjection, and the like.

Vectors for introducing heterologous (i.e., foreign) nucleic acid (DNA or RNA) into muscle cells for the expression of bioactive products are well known in the art. Such vectors possess a promoter sequence, preferably, a promoter that is cell-specific and placed upstream of the sequence to be expressed. The vectors may also contain, optionally, one or more expressible marker genes for expression as an indication of successful transfection and expression of the nucleic acid sequences contained in the vector.

Illustrative examples of vehicles or vector constructs for transfection or infection of the muscle-derived cells of the present invention include replication-defective viral vectors, DNA virus or RNA virus (retrovirus) vectors, such as adenovirus, herpes simplex virus and adeno-associated viral vectors. Adeno-associated virus vectors are single stranded and allow the efficient delivery of multiple copies of nucleic acid to the cell's nucleus. Preferred are adenovirus vectors. The vectors will normally be substantially free of any prokaryotic DNA and may comprise a number of different functional nucleic acid sequences. Examples of such functional sequences include polynucleotide, e.g., DNA or RNA, sequences comprising transcriptional and translational initiation and termination regulatory sequences, including promoters (e.g., strong promoters, inducible promoters, and the like) and enhancers which are active in muscle cells.

Also included as part of the functional sequences is an open reading frame (polynucleotide sequence) encoding a protein of interest; flanking sequences may also be included for site-directed integration. In some situations, the 5'-flanking sequence will allow homologous recombination, thus changing the nature of the transcriptional initiation region, so as to provide for inducible or noninducible transcription to increase or decrease the level of transcription, as an example.

In general, the nucleic acid sequence desired to be expressed by the muscle-derived progenitor cell is that of a structural gene, or a functional fragment, segment or portion of the gene, that is heterologous to the muscle-derived progenitor cell and encodes a desired protein or polypeptide product, for example. The encoded and expressed product may be intracellular, i.e., retained in the cytoplasm, nucleus, or an organelle of a cell, or may be secreted by the cell. For secretion, the natural signal sequence present in the structural gene may be retained, or a signal sequence that is not naturally present in the structural gene may be used. When the polypeptide or peptide is a fragment of a protein that is larger, a signal sequence may be provided so that, upon secretion and processing at the processing site, the desired protein will have the natural sequence. Examples of genes of interest for use in accordance with the present invention include genes encoding cell growth factors, cell differentiation factors, cell signaling factors and programmed cell death factors. Specific examples include, but are not limited to, genes encoding BMP-2 (rhBMP-2), IL-1Ra, Factor IX, and connexin 43.

As mentioned above, a marker may be present for selection of cells containing the vector construct. The marker may be an inducible or non-inducible gene and will generally allow for positive selection under induction, or without induction, respectively. Examples of commonly-used marker genes include neomycin, dihydrofolate reductase, glutamine synthetase, and the like.

The vector employed will generally also include an origin of replication and other genes that are necessary for replication in the host cells, as routinely employed by those having skill in the art. As an example, the replication system comprising the origin of replication and any proteins associated with replication encoded by a particular virus may be included as part of the construct. The replication system must be selected so that the genes encoding products necessary for replication do not ultimately transform the muscle-derived cells. Such replication systems are represented by replication-defective adenovirus constructed as described, for example, by G. Acsadi et al, 1994, *Hum. Mol. Genet.* 3:579-584, and by Epstein-Barr virus. Examples of replication defective vectors, particularly, retroviral vectors that are replication defective, are BAG, described by Price et al., 1987, *Proc. Natl. Acad. Sci. USA*, 84:156; and Sanes et al., 1986, *EMBO J.,* 5:3133. It will be understood that the final gene construct may contain one or more genes of interest, for example, a gene encoding a bioactive metabolic molecule. In addition, cDNA, synthetically produced DNA or chromosomal DNA may be employed utilizing methods and protocols known and practiced by those having skill in the art.

If desired, infectious replication-defective viral vectors may be used to genetically engineer the cells prior to In vivo injection of the cells. In this regard, the vectors may be introduced into retroviral producer cells for amphotrophic packaging. The natural expansion of muscle-derived progenitor cells into adjacent regions obviates a large number of injections into or at the site(s) of interest.

In another aspect, the present invention provides ex vivo gene delivery to cells and tissues of a recipient mammalian host, including humans, through the use of MDCs, e.g., early progenitor muscle cells, that have been virally transduced using an adenoviral vector engineered to contain a heterologous gene encoding a desired gene product. Such an ex vivo approach provides the advantage of efficient viral gene transfer, which is superior to direct gene transfer approaches. The ex vivo procedure involves the use of the muscle-derived progenitor cells from isolated cells of muscle tissue. The muscle biopsy that will serve as the source of muscle-derived progenitor cells can be obtained from an injury site or from another area that may be more easily obtainable from the clinical surgeon.

It will be appreciated that in accordance with the present invention, clonal isolates can be derived from the population of muscle-derived progenitor cells (i.e., PP6 cells or slowly adhering cells) using various procedures known in the art, for example, limiting dilution plating in tissue culture medium. Clonal isolates comprise genetically identical cells that originate from a single, solitary cell. In addition, clonal isolates can be derived using FACS analysis as described above, followed by limiting dilution to achieve a single cell per well to establish a clonally isolated cell line.

The MDCs are first infected with engineered viral vectors containing at least one heterologous gene encoding a desired gene product, suspended in a physiologically acceptable carrier or excipient, such as saline or phosphate buffered saline, and then administered to an appropriate site in the host. Consistent with the present invention, the MDCs can be administered to body tissues, including bone, epithelial tissue, connective tissue, muscle tissue, and various organ tissues such as those organs that are associated with the digestive system, cardiovascular system, respiratory system, reproductive system, urological system, and nervous system, as described above. The desired gene product is expressed by the injected cells, which thus introduce the gene product into the host. The introduced and expressed gene products can thereby be utilized to treat, repair, or ameliorate the injury, dysfunction, or disease, due to their being expressed over long time periods by the MDCs of the invention, having long-term survival in the host.

In animal model studies of myoblast-mediated gene therapy, implantation of $10^6$ myoblasts per 100 mg muscle was required for partial correction of muscle enzyme defects (see, J. E. Morgan et al., 1988, *J. Neural. Sci.* 86:137; T. A. Partridge et al., 1989, *Nature* 337:176). Extrapolating from this data, approximately $10^{12}$ MDCs suspended in a physiologically compatible medium can be implanted into muscle tissue for gene therapy for a 70 kg human. This number of MDCs of the invention can be produced from a single 100 mg skeletal muscle biopsy from a human source (see below). For the treatment of a specific injury site, an injection of genetically engineered MDCs into a given tissue or site of injury comprises a therapeutically effective amount of cells in solution or suspension, preferably, about $10^5$ to $10^6$ cells per $cm^3$ of tissue to be treated, in a physiologically acceptable medium.

EXAMPLES

Example 1

MDC Enrichment, Isolation and Analysis According to the Pre-Plating Method

Enrichment and isolation of MDCs: MDCs were prepared as described (U.S. Pat. No. 6,866,842 of Chancellor et al.). Muscle explants were obtained from the hind limbs of a number of sources, namely from 3-week-old mdx (dystrophic) mice (C57BL/10ScSn mdx/mdx, Jackson Laboratories), 4-6 week-old normal female SD (Sprague Dawley) rats, or SCID (severe combined immunodeficiency) mice. The muscle tissue from each of the animal sources was dissected to remove any bones and minced into a slurry. The slurry was then digested by 1 hour serial incubations with 0.2% type XI collagenase, dispase (grade II, 240 unit), and 0.1% trypsin at 37° C. The resulting cell suspension was passed through 18, 20, and 22 gauge needles and centrifuged at 3000 rpm for 5 minutes. Subsequently, cells were suspended in growth medium (DMEM supplemented with 10% fetal bovine serum, 10% horse serum, 0.5% chick embryo extract, and 2% penicillin/streptomycin). Cells were then preplated in collagen-coated flasks (U.S. Pat. No. 6,866,842 of Chancellor et al.). After approximately 1 hour, the supernatant was removed from the flask and re-plated into a fresh collagen-coated flask. The cells which adhered rapidly within this 1 hour incubation were mostly fibroblasts (Z. Qu et al., supra; U.S. Pat. No. 6,866,842 of Chancellor et al.). The supernatant was removed and re-plated after 30-40% of the cells had adhered to each flask. After approximately 5-6 serial platings, the culture was enriched with small, round cells, designated as PP6 cells, which were isolated from the starting cell population and used in further studies. The adherent cells isolated in the early platings were pooled together and designated as PP1-4 cells.

The mdx PP1-4, mdx PP6, normal PP6, and fibroblast cell populations were examined by immunohistochemical analysis for the expression of cell markers. The results of this analysis are shown in Table 1.

TABLE 1

| Cell markers expressed in PP1-4 and PP6 cell populations. | | | | |
|---|---|---|---|---|
| | mdx PP1-4 cells | mdx PP6 cells | nor PP6 cells | fibroblasts |
| desmin | +/− | + | + | − |
| CD34 | − | + | + | − |
| Bcl-2 | (−) | + | + | − |
| Flk-1 | na | + | + | − |
| Sca-1 | na | + | + | − |
| M-cadherin | −/+ | −/+ | −/+ | − |
| MyoD | −/+ | +/− | +/− | − |
| myogenin | −/+ | +/− | +/− | − |

Mdx PP1-4, mdx PP6, normal PP6, and fibroblast cells were derived by preplating technique and examined by immunohistochemical analysis. "−" indicates less than 2% of the cells showed expression; "(−)"; "−/+" indicates 5-50% of the cells showed expression; "+/−" indicates ~40-80% of the cells showed expression; "+" indicates that >95% of the cells showed expression; "nor" indicates normal cells; "na" indicates that the immunohistochemical data is not available.

It is noted that both mdx and normal mice showed identical distribution of all of the cell markers tested in this assay. Thus, the presence of the mdx mutation does not affect the cell marker expression of the isolated PP6 muscle-cell derived population.

MDCs were grown in proliferation medium containing DMEM (Dulbecco's Modified Eagle Medium) with 10% FBS (fetal bovine serum), 10% HS (horse serum), 0.5% chick embryo extract, and 1% penicillin/streptomycin, or fusion medium containing DMEM supplemented with 2% fetal bovine serum and 1% antibiotic solution. All media supplies were purchased through Gibco Laboratories (Grand Island, N.Y.).

Example 2

MDC Enrichment, Isolation and Analysis According to the Single Plate Method

Enrichment and Isolation of MDCs

Populations of rapidly- and slowly-adhering MDCs were isolated from skeletal muscle of a mammalian subject. The subject may be a human, rat, dog or other mammal. Biopsy size ranged from 42 to 247 mg.

Skeletal muscle biopsy tissue was immediately placed in cold hypothermic medium (HYPOTHERMOSOL® (BioLife) supplemented with gentamicin sulfate (100 ng/ml, Roche)) and stored at 4° C. After 3 to 7 days, biopsy tissue was removed from storage and production was initiated. Any connective or non-muscle tissue was dissected from the biopsy sample. The remaining muscle tissue that was used for isolation is weighed. The tissue was minced in Hank's Balanced Salt Solution (HBSS), transferred to a conical tube, and centrifuged (2,500×g, 5 minutes). The pellet was then resuspended in a Digestion Enzyme solution (Liberase Blendzyme 4 (0.4-1.0 U/mL, Roche)). 2 mL of Digestion Enzyme solution was used per 100 mg of biopsy tissue and was incubated for 30 minutes at 37° C. on a rotating plate. The sample was then centrifuged (2,500×g, 5 minutes). The pellet was resuspended in culture medium and passed through a 70 μm cell strainer. The culture media used for the procedures described in this Example was Cambrex Endothelial Growth Medium EGM-2 basal medium supplemented with the following components: i. 10% (v/v) fetal bovine serum, and ii. Cambrex EGM-2 SingleQuot Kit, which contains: Insulin Growth Factor-1 (IGF-1), Basic Fibroblast Growth Factor (bFGF), Vascular Endothelial Growth Factor (VEGF), Epidermal Growth Factor (EGF), Hydrocortisone, Heparin, and Ascorbic Acid. The filtered cell solution was then transferred to a T25 culture flask and incubated for 30-120 minutes at 37° C. in 5% $CO_2$. Cells that attached to this flask were termed the "rapidly-adhering cells".

After incubation, the cell culture supernatant was removed from the T25 flask and placed into a 15 mL conical tube. The T25 culture flask is rinsed with 2 mL of warmed culture medium and transferred to the aforementioned 15 mL conical tube. The 15 mL conical tube is centrifuged (2,500×g, 5 minutes). The pellet was resuspended in culture medium and transferred to a new T25 culture flask. The flask was incubated for ~2 days at 37° C. in 5% CO2 (cells that attach to this flask were termed the "slowly-adhering cells"). After incubation, the cell culture supernatant was aspirated and new culture medium was added to the flask. The flask was then returned to the incubator for expansion. Standard culture passaging is carried out from here on to maintain the cell confluency in the culture flask at less than 50%. Trypsin-EDTA (0.25%, Invitrogen) was used to detach the adherent cells from the flask during passage. Typical expansion of the "slowly-adhering cells" took an average of 17 days (starting from the day production is initiated) to achieve an average total viable cell number of 37 million cells.

Once the desired cell number was achieved, the cells were harvested from the flask using Trypsin-EDTA and centrifuged (2,500×g, 5 minutes). The pellet was resuspended in BSS-P solution (HBSS supplemented with human serum albumin (2% v/v, Sera Care Life)) and counted. The cell solution was then centrifuged again (2,500×g, 5 minutes), resuspended with Cryopreservation Medium (CRYOSTOR™ (Biolife) supplemented with human serum albumin (2% v/v, Sera Care Life Sciences)) to the desired cell concentration, and packaged in the appropriate vial for cryogenic storage. The cryovial was placed into a freezing container and placed in the −80° C. freezer. Cells were administered by thawing the frozen cell suspension at room temperature with an equal volume of physiologic saline and injected directly (without additional manipulation). The lineage characterization of the slowly adhering cell populations showed: Myogenic (87.4% CD56+, 89.2% desmin+), Endothelial (0.0% CD31+), Hematopoietic (0.3% CD45+), and Fibroblast (6.8% CD90+/CD56−).

Analysis for Characterization of Enriched and Isolated MDCs

Following disassociation of the skeletal muscle biopsy tissue, two fractions of cells were collected based on their rapid or slow adhesion to the culture flasks, as described above. The cells were then expanded in culture with growth medium and then frozen in cryopreservation medium ($3 \times 10^5$ cells in 15 μl) in a 1.5 ml eppendorf tube, also as described above. For the control group, 15 μl of cryopreservation medium alone was placed into the tube. These tubes were stored at −80° C. until injection. Immediately prior to injection, a tube was removed from storage, thawed at room temperature, and resuspended with 15 μl of 0.9% sodium chloride solution. The resulting 30 μl solution was then drawn into a 0.5 cc insulin syringe with a 30 gauge needle. The investigator performing the surgery and injection was blinded to the contents of the tubes.

Cell count and viability was measured using a Guava flow cytometer and Viacount assay kit (Guava). CD56 was measured by flow cytometry (Guava) using PE-conjugated anti-CD56 antibody (1:50, BD Pharmingen) and PE-conjugated isotype control monoclonal antibody (1:50, BD Pharmingen). Desmin was measured by flow cytometry (Guava) on paraformaldehyde-fixed cells (BD Pharmingen) using a monoclonal desmin antibody (1:100, Dako) and an isotype control monoclonal antibody (1:200, BD Pharmingen). Fluorescent labeling was performed using a Cy3-conjugated anti-mouse IgG antibody (1:250, Sigma). In between steps, the cells were washed with permeabilization buffer (BD Pharmingen). For creatine kinase (CK) assay, $1 \times 10^5$ cells were plated per well into a 12 well plate in differentiation-inducing medium. Four to 6 days later, the cells were harvested by trypsinization and centrifuged into a pellet. The cell lysis supernatant was assayed for CK activity using the CK LIQUI-UV® kit (Stanbio).

Example 3

Treatment of Urinary Incontinence with Human MDCs in a Rat Model

Treatment with human MDCs led to restoration of leak point pressure (LPP) back to normal levels in an experimental model of stress urinary incontinence (SUI). Injected human MDCs alleviated urinary incontinence in a well established rat model.

These experiments demonstrate proof of concept and feasibility of using human cell therapy for urologic application. The human MDCs were harvested from a clinically-obtainable sized muscle biopsy, and improved physiologic outcomes for up to four weeks in an immunocompromised rat model of SUI. Histologic evaluation demonstrated periurethral muscle atrophy in the sham group only. Human MDCs were present in the nude rat urethral sphincter 4 weeks after injection. Treatment with human MDCs led to restoration of LPP back to near-normal levels in an experimental model of SUI in the nude rat.

Animals: The experiments described below were performed using 6-8 week old female, athymic nude rats (Hsd: RH-rnu, Harlan Laboratory). Procedural protocols were approved by the Animal Research Care Committee of Children's Hospital of Pittsburgh. The policies and procedures of the animal laboratory are in accordance with those detailed in the guide for the 'Care and Use of Laboratory Animals' published by the US Department of Health and Human Services.

Denervation of sciatic nerve (SUI model): A well-established SUI model was created through bilateral transection of the sciatic nerve. Rats were given isoflurane anesthesia (2 L/min) and, after appropriate induction, bilateral vertical dorsal incisions were performed over the ischiorectal fossa. Under an operating microscope, the sciatic nerve on each side was identified and 2 mm of those trunks were excised distal to its origin from the vertebral column, but proximal to the branching of the pudendal nerve.

Human MDC isolation: Human MDCs used in this study were isolated from human skeletal muscle tissue (~250 mg) harvested from the rectus abdominus of a single donor, and isolated according to the single plate technique described above. Culture expansion was carried out in an antibiotic-free proprietary medium supplemented with 10% fetal bovine serum. Flow cytometric analysis of the MDC suspensions was performed to evaluate myogenic content through antibody labeling of CD56 expression (BD Pharmingen). MDCs were cryopreserved at a concentration of $1\times10^6$ viable cells/10 µL. Separate aliquots of carrier medium alone were also prepared for sham injection.

Injection Procedure: Seven days following denervation, under isoflurane anesthesia (2 L/min), a low midline incision was made to expose the bladder and urethra. Cryopreserved MDCs or sham suspensions were thawed with an equal volume of saline just prior to injection. A 3/10-mL insulin syringe was used to inject either 10 µL ($5\times10^5$ cells) of MDC suspension or sham aliquot into each lateral wall of the mid-urethra with microscopic guidance. Non-denervated, non-injected, age-matched animals served as controls.

In Vivo Cystometry (CMG) and Leak Point Pressure (LPP) Measurement: In vivo functional measurements were performed 4 weeks following injections. Under urethane anesthesia (1.2 g/kg subcutaneous injection), a midline abdominal incision was made and the ureters were ligated. A transvesical catheter with a fire-flared tip (PE-90) was inserted into the dome of the bladder for bladder filling and pressure recording, and the abdomen was closed. A three-way stopcock was connected to the transvesical tube to monitor the bladder pressure during cystometry (continuous infusion of normal saline at rate of 0.04 mL/min). The voided volume, bladder capacity and maximal voiding pressure were monitored. After cystometry, all rats underwent spinal cord transection at the T9 level in order to eliminate spontaneous bladder activity in response to increasing intravesical pressures. The rats were then mounted on a tilt table and placed in the vertical position. Intravesical pressure was clamped by connecting a large 50 mL syringe to the bladder catheter and the pressure transducer via PE-190 tubing and three-way stopcocks. The reservoir was mounted on a metered vertical pole for controlled height adjustment. Intravesical pressure was increased in 1-3 cmH$_2$O steps from zero upward until visual identification of leakage; this pressure was identified as the LPP. Three consecutive readings were obtained and averaged for each animal and presented as a single LPP.

Tissue Harvest and Histology: Immediately following the LPP measurement, the entire urethra-bladder complex was removed. The tissues were snap frozen using 2-methylbutane precooled in liquid nitrogen. Cryosections of the urethra were labeled with hematoxylin/eosin (H&E) for general histology, and also immunofluorescently-labeled with human specific anti-lamins A/C antibody (Novocastra, U.K.) to follow the fate of the injected MDC.

Statistical Analysis: Data are presented as means±SE. Overall comparisons between groups were performed using a one-way analysis of variance (Tukey's multiple comparison test). A p-value of less than 0.05 was accepted as significant.

The injected MDC suspensions contained 87.7% myogenic (CD56-positive) cells; the remainders of the cells were fibroblastic. There were no serious adverse effects observed in any rat in the control, sham and MDC-injected groups. However, partial obstruction of the external urethral meatus due to infection at the perineal area was found in one animal each in both the sham and human MDC-injected groups. Thus, these animals were excluded from the functional analysis.

CMG and LPP Measurement: No difference in any measured cystometric parameter was observed between the control, sham and human MDC-injected groups (Table 2).

TABLE 2

| Cystometric variables in each group. | | | | |
|---|---|---|---|---|
| Cystometric parameters | Control | Sham | MDC | P-value |
| Maximal voiding pressure (cmH$_2$O) | 29.8 ± 1.4 | 29.3 ± 2.8 | 33.7 ± 5.8 | 0.677 |
| Bladder capacity (ml) | 0.40 ± 0.06 | 0.36 ± 0.09 | 0.34 ± 0.03 | 0.827 |

Figure 1:
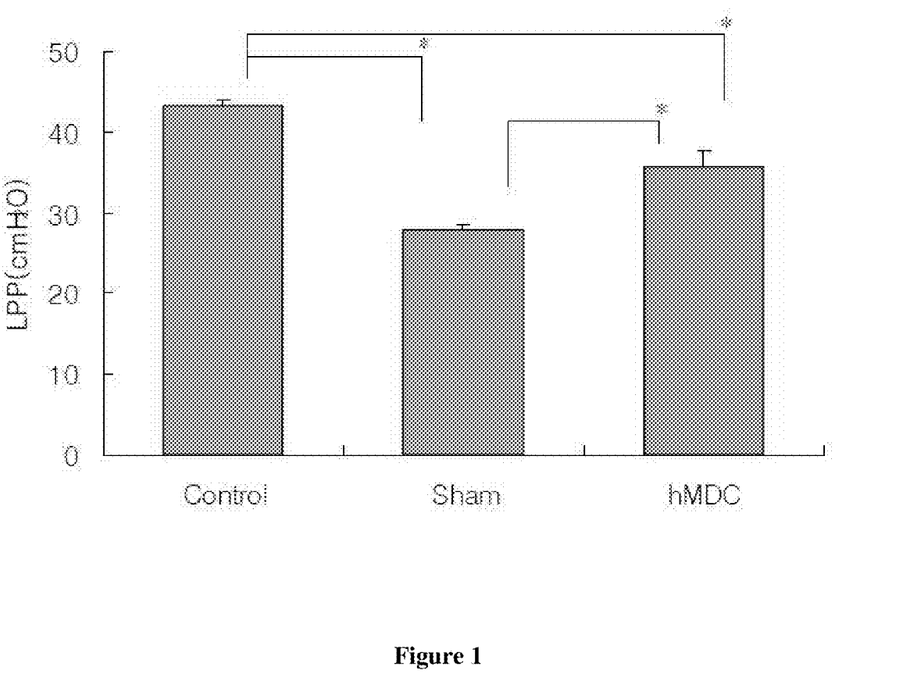
FIG. 1 is a bar graph showing higher leak point pressure in rats treated with human MDCs than control.

Denervation of the urethral sphincter resulted in a significant decrease in LPP from the control to sham groups (FIG. 1) (43.4±0.6 to 27.8+0.7 cmH$_2$O, respectively; p<0.05). LPP was restored to significantly higher levels following MDC injection (35.7±2.0 cmH$_2$O) when compared to the sham group (p<0.05); however, at the 4 week time point, this level of restoration remained significantly less than that of control group (p<0.05).

Figure 2A:
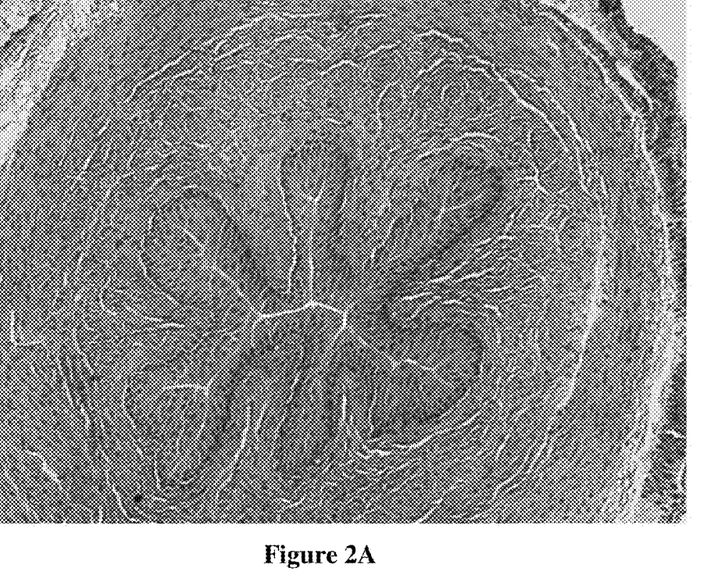
FIG. 2A is a light micrograph of a proximal urethral sphincter in a control rat.
Figure 2B:
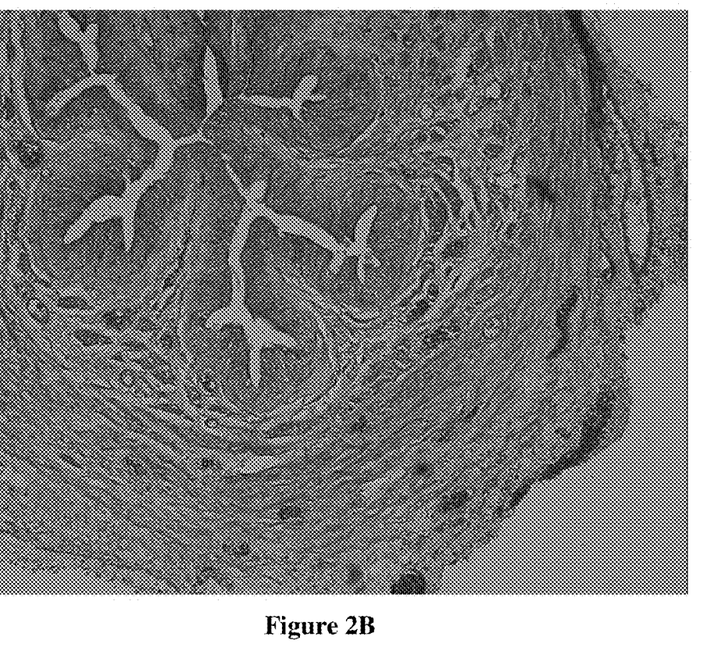
FIG. 2B is a light micrograph of a proximal urethral sphincter in a rat treated with human MDCs.
Figure 3:
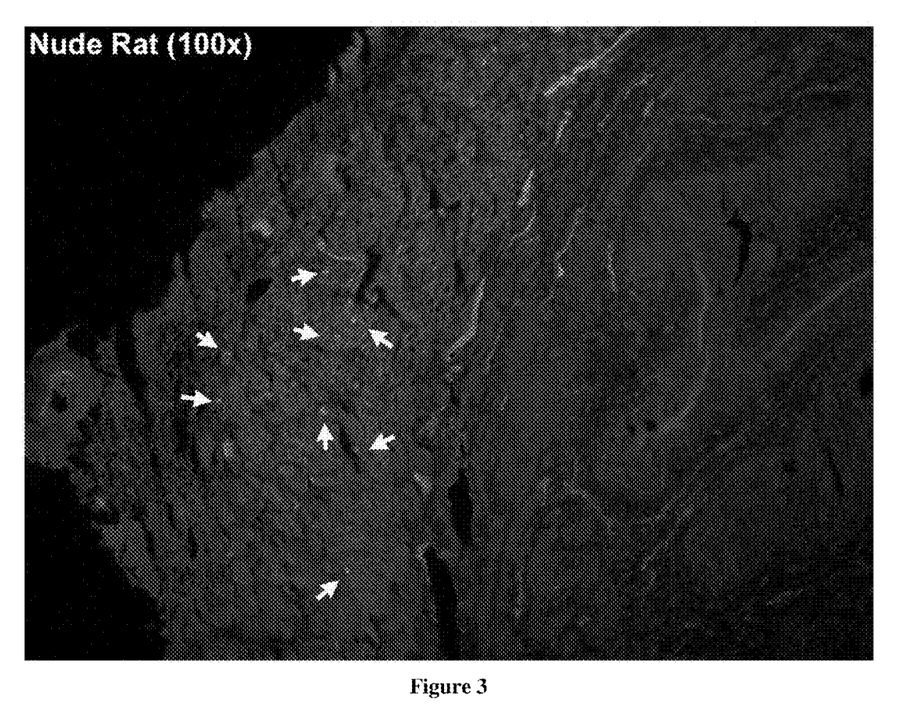
FIG. 3 shows immunofluorescent labeling with a human-specific nuclear antibody (lamins A/C) revealing the presence of human nuclei incorporated within the striated sphincter muscle layer in human MDC injected tissue (100×). Arrows point to individual nuclei.

Histological Analysis: In the denervated rats, the proximal urethral sphincter was atrophic at 4 weeks compared with control (FIG. 2). Human nuclei present within the rat sphincter tissue was revealed through immunofluorescent labeling using a human-specific antibody to the nuclear envelope proteins lamins A and C. Tissues from the MDC-injected group showed clear positive labeling of numerous human nuclei incorporated within the external (striated) sphincter muscle (FIG. 3).

All patent applications, patents, texts, and literature references cited in this specification are hereby incorporated herein by reference in their entirety to more fully describe the state of the art to which the present invention pertains.

As various changes can be made in the above methods and compositions without departing from the scope and spirit of the invention as described, it is intended that all subject matter contained in the above description, shown in the accompanying drawings, or defined in the appended claims be interpreted as illustrative, and not in a limiting sense.

We claim:

1. A method of treating a urinary tract disease in a mammalian subject in need thereof comprising:
   (a) isolating skeletal muscle cells from a human,
   (b) cooling the cells to a temperature lower than 10° C. and storing the cells for 1-7 days;
   (c) suspending the human skeletal muscle cells in a first cell culture container for between 30 and 120 minutes;
   (d) decanting the medium from the first cell culture container into a second cell culture container;
   (e) allowing the remaining cells in the medium in the second container to attach to the walls of the second cell culture container;
   (f) isolating the cells from the walls of the second cell culture container, wherein the isolated cells are muscle derived progenitor cells (MDCs);
   (g) culturing the MDCs isolated in step (f) to expand their number;

(h) freezing the MDCs prepared in step (g) to a temperature below −30 °C.; and (i) thawing the MDCs prepared in step (h) and administering the thawed MDCs to the urinary tract of the mammalian subject; thereby, treating urinary tract disease in a mammalian subject in need thereof.

2. The method of claim 1, wherein the mammalian subject is a human.

3. The method of claim 2, wherein the human skeletal muscle cells are isolated from the human subject before the urinary tract disease begins in the human subject.

4. The method of claim 2, wherein the human skeletal muscle cells are isolated from the human subject after the urinary tract disease begins in the human subject.

5. The method of claim 1, wherein the MDCs are administered by injecting them into the urethra.

6. The method of claim 1, wherein the MDCs are injected into the periurethral muscle.

7. The method of claim 1, wherein the urinary tract disease is urinary incontinence.

8. The method of claim 6, wherein the urinary incontinence is stress urinary incontinence.

9. A method of improving at least one symptom associated with urinary tract disease in a mammalian subject in need thereof comprising:

(a) isolating skeletal muscle cells from a human, (b) suspending the human skeletal muscle cells in a first cell culture container for between 30 and 120 minutes;

(c) decanting the medium from the first cell culture container into a second cell culture container;

(d) allowing the remaining cells in the medium in the second container to attach to the walls of the second cell culture container;

(e) isolating the cells from the walls of the second cell culture container, wherein the isolated cells are MDCs; and (f) administering the MDCs obtained in step (e) to the urinary tract of the mammalian subject; thereby, improving at least one symptom associated with urinary tract disease in a mammalian subject in need thereof.

10. The method of claim 9, wherein the symptom is selected from the group consisting of urinary incontinence, urinary tract infection, frequent urination, painful urination, burning sensation when urinating, fatigue, tremor, cloudy urine, blood in urine, and kidney infection.

11. The method of claim 9, wherein the MDCs are administered by injecting them into the urethra.

12. The method of claim 11, wherein the MDCs are injected into the periurethral muscle.

13. The method of claim 9, wherein the mammal is a human.

14. The method of claim 9, wherein the MDCs are cultured to expand their number before being administered to the urinary tract of the mammalian subject.

15. A method of treating a urinary tract disease in a mammalian subject in need thereof comprising administering a cell population containing muscle-derived cells (MDCs) to the urinary tract of the mammalian subject, wherein the cell population containing MDCs has been obtained by a process comprising:

(a) isolating skeletal muscle cells from a mammal;

(b) cooling the cells to a temperature lower than 10° C. and storing the cells for 1-7 days;

(c) suspending the cells obtained in step (b) in a first cell culture container for a duration sufficient to adhere a first cell population to the container, wherein a second cell population remains in the culture medium and not adhered to the first container;

(d) transferring the culture medium comprising the second cell population from the first cell culture container into a second cell culture container;

(e) allowing cells from the second cell population to attach to the second cell culture container;

(f) isolating the cells attached to the second cell culture container to obtain said cell population containing MDCs; and (g) administering a therapeutically effective amount of the MDCs prepared in step (d) to the urinary tract of the mammalian subject.

* * * * *